United States Patent [19]
Bray, Jr.

[11] Patent Number: 5,888,223
[45] Date of Patent: Mar. 30, 1999

[54] ANTERIOR STABILIZATION DEVICE

[76] Inventor: Robert S. Bray, Jr., 28660 Wagon Rd., Agoura, Calif. 91305

[21] Appl. No.: 95,007

[22] Filed: Jun. 9, 1998

Related U.S. Application Data

[63] Continuation of Ser. No. 764,089, Dec. 6, 1996, abandoned.

[60] Provisional application No. 60/008,365, Dec. 8, 1995.

[51] Int. Cl.⁶ .................................................... A61B 17/70
[52] U.S. Cl. .............................................. 623/17; 606/61
[58] Field of Search ................................ 606/61, 60, 72, 606/73; 623/17

[56] References Cited

U.S. PATENT DOCUMENTS

| | | | |
|---|---|---|---|
| 3,426,364 | 2/1969 | Lumb | 606/61 |
| 4,599,086 | 7/1986 | Doty | 623/17 |
| 4,892,545 | 1/1990 | Day et al. | 623/17 |
| 4,904,261 | 2/1990 | Dove et al. | 623/17 |
| 4,917,704 | 4/1990 | Frey et al. | 623/17 |
| 4,955,908 | 9/1990 | Frey et al. | 623/17 |
| 5,123,926 | 6/1992 | Pisharodi | 623/17 |
| 5,397,364 | 3/1995 | Kozak et al. | 623/17 |
| 5,458,638 | 10/1995 | Kuslich et al. | 623/17 |
| 5,458,641 | 10/1995 | Jimenez | 623/17 |
| 5,522,899 | 6/1996 | Michelson | 623/17 |

FOREIGN PATENT DOCUMENTS

179695 A1   4/1986   European Pat. Off. .

OTHER PUBLICATIONS

Advertisement for Orion, "Anterior Cerical Plate System", Danek Medical, Inc., 1994.

*Primary Examiner*—Guy V. Tucker
*Attorney, Agent, or Firm*—Christie, Parker & Hale, LLP

[57] ABSTRACT

An anterior fixation device comprises an oval shaped intervertebral spacer and a retaining plate. The spacer has a side wall and superior and inferior walls. The superior and inferior walls are dome-shaped and porous to allow bone to grow through the device to achieve fusion of two adjacent vertebral bodies. Extending from the anterior side of the spacer are superior and inferior lips through which bone screws 16 extend. The bone screws are non-weight bearing and screw into the strongest areas of bone within the vertebral bodies. The intervertebral spacer is hollow inside to allow for bone grafts, bone morphogenic protein, or other bone stimulating substances to be inserted therein. The retaining plate is attachable to the anterior surface of the spacer to prevent the bone screws from backing out once the device is installed.

13 Claims, 10 Drawing Sheets

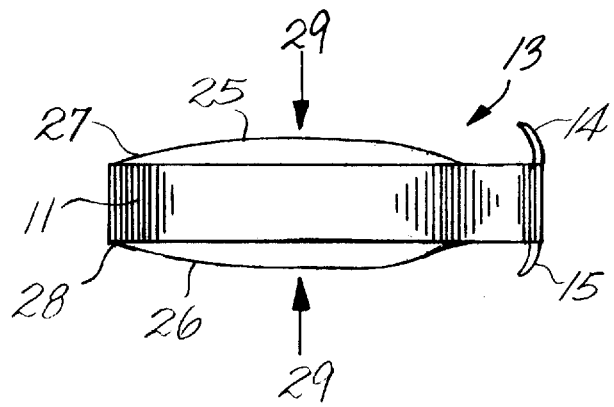
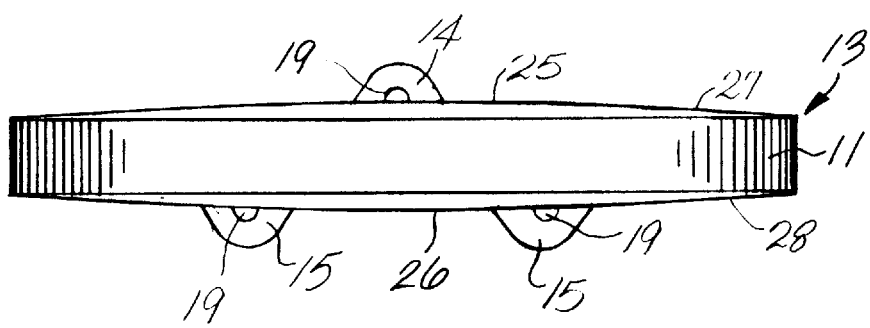

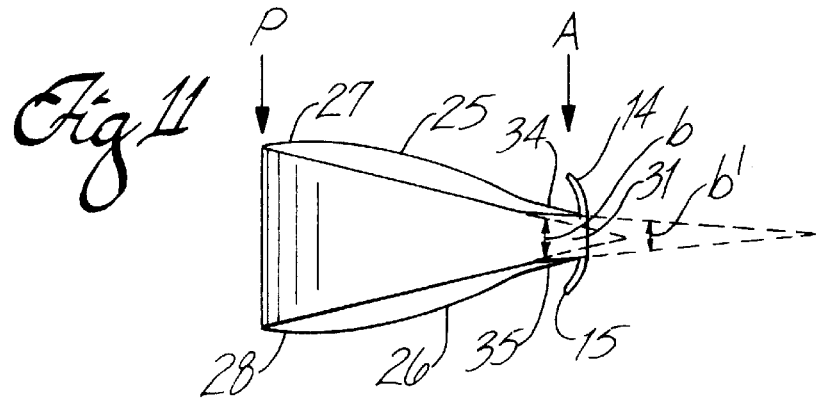
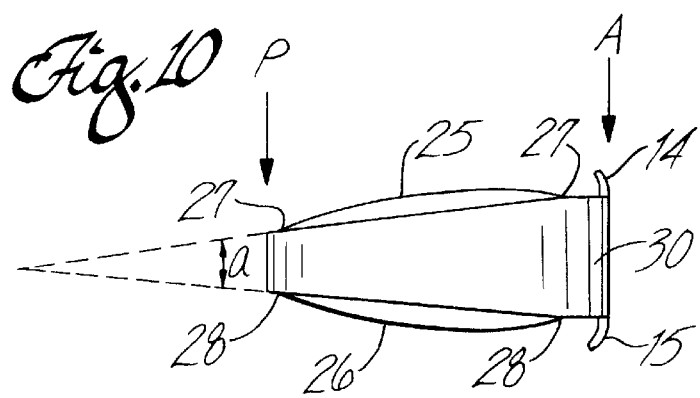
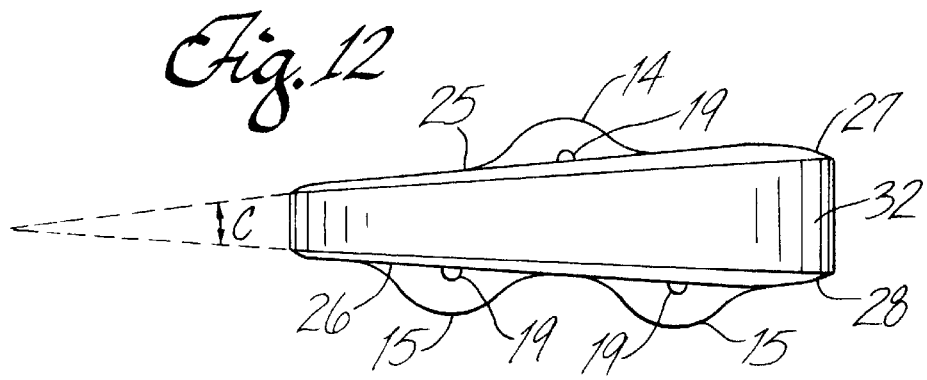
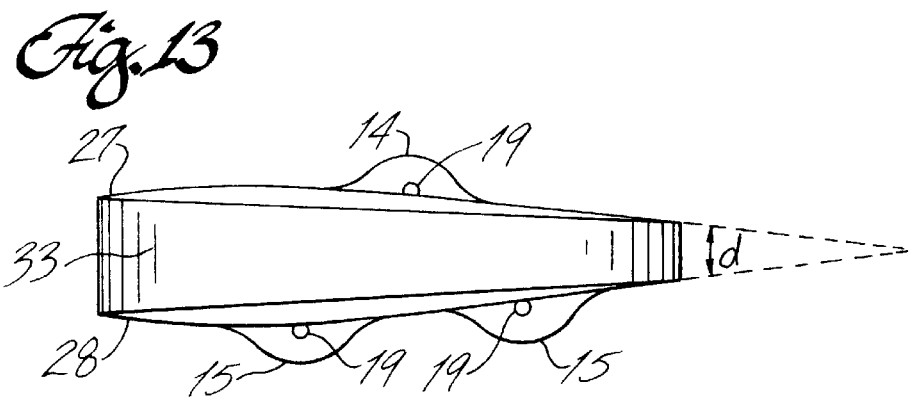

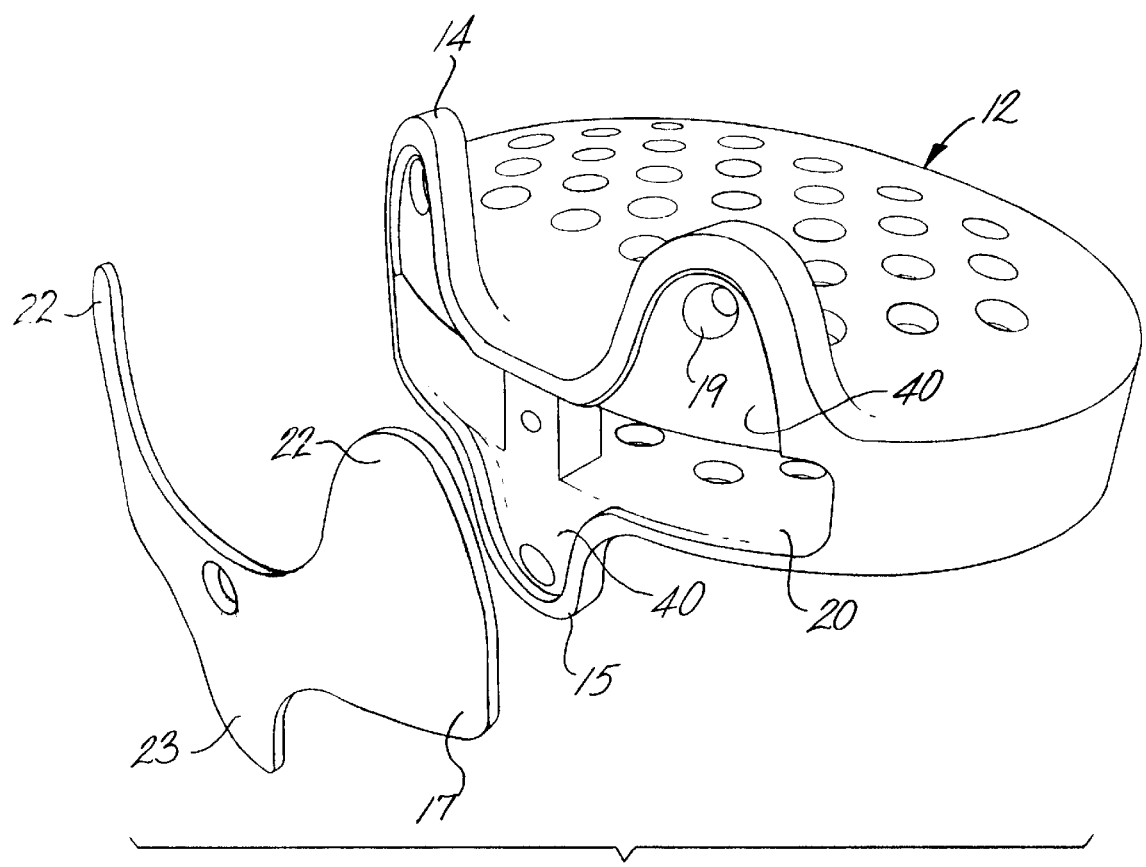

ANTERIOR STABILIZATION DEVICE

CROSS-REFERENCE TO RELATED APPLICATIONS

This application in a continuation of U.S. application Ser. No. 08/764,089, filed Dec. 6, 1996, now abandoned, which claims priority of Provisional Application Ser. No. 60/008,365, filed Dec. 8, 1995.

FIELD OF THE INVENTION

The present invention relates to a device for stabilizing and/or fusing at least two adjacent vertebrae of a spine. More specifically, the present invention relates to a device that is placed on the anterior surface and in the intervertebral space of two adjacent vertebral bodies to thereby fix the spacial relationship of the vertebral bodies to achieve stabilization and/or bone fusion.

BACKGROUND OF THE INVENTION

The spinal column of humans provides support to the body and protection to the delicate spinal cord and nerves. The spinal column comprises a series of vertebrae stacked on top of each other. Each vertebra has a relatively large vertebral body that is located in the anterior portion of the spine and provides the majority of the weight bearing support of the vertebral column. Each vertebral body has relatively strong bone comprising the outside surface of the body and weak bone comprising the center of the body. Situated between each vertebral body is an intervertebral disc that provides for cushioning and dampening of compressive forces to the sinal column. Located just posterior to the vertebral body and intervertebral disc is the vertebral canal containing the delicate sinal cord and nerves. Posterior to the spinal canal are the different articulating processes of the vertebra.

Various types of spinal column disorders are known and include scoliosis (abnormal lateral curvature of the spine), kyphosis (abnormal forward curvature of the spine, usually in the thoracic spine), excess lordosis (abnormal backward curvature of the spine, usually in the lumbar spine), spondylolisthesis (forward displacement of one vertebra over another, usually in the lumbar or cervical spine) and other disorders, such as ruptured or slipped discs, degenerative disc disease, fractured vertebra, and the like. Patients who suffer from such conditions usually experience extreme and debilitating pain and often neurologic deficit in nerve function.

A technique known as spinal fixation uses surgical implants which mechanically immobilize areas of the spine assisting in the eventual fusion of the treated adjacent vertebrae. Such techniques have been used effectively to treat the above described conditions and, in most cases, to relieve pain suffered by the patient. However, there are some disadvantages to the present fixation devices.

One technique for spinal fixation includes the immobilization of the spine by the use of spine rods that run generally parallel to the spine. In practicing this technique, the posterior surface of the spine is isolated and bone screws are first fastened to the pedicles of the appropriate vertebrae or to the sacrum and act as anchor points for the spine rods. The bone screws are generally placed two per vertebra, one at each pedicle on either side of the spinous process. Clamp assemblies join the spine rods to the screws. The spine rods are generally bent to achieve the desired curvature of the spinal column. These types of systems are very stable but require implanting screws into each vertebra over the area to be treated. Also, since the pedicles of vertebrae above the second lumbar vertebra (L2) are very small, only small bone screws can be used which sometimes do not give the needed support to stabilize the spine. To stabilize the implanted system sufficiently, one vertebra above and one vertebra below the area to be treated are often used for implanting pedicle screws. The rods and clamps are surgically fixed to the spine from a posterior approach.

Anterior fixation devices have also been used such as anterior plate systems. One type of anterior plate system involves a titanium plate with unicortical titanium bone screws that lock to the plate and are placed over the anterior surface of a vertebral body. Another type of anterior plate system used less frequently nowadays involves the use of bicortical screws that do not lock to the plate. The bone screws have to be long enough to bite into both sides of the vertebral body (cortex) to gain enough strength to obtain the needed stability. These devices are difficult to place due to the length of the screws and damage occurs when the screws are misplaced.

A third type of anterior fixation device comprises a hollow cylinder, usually a hollow cylindrical titanium cage, that is externally threaded. The externally threaded cage is screwed into place between to adjacent vertebrae. Bone grafts from cadavers or the pelvis are then packed into the hollow center of the device. Bone morphogenic protein (which is not yet commercially available) or other substances that promote bone growth can also be placed in the hollow center of the device. The cage is porous such that bone can grow through the device and fuse the two adjacent vertebrae. The are many disadvantages to this device. First, it is very difficult to align. Second, it requires drilling a large hole between two adjacent vertebral bodies and then threading the device into the hole. The large hole can compromise the integrity of the vertebral bodies, and if drilled too posteriorly, can injure the spinal cord. Third, the end plates of the vertebral bodies are usually destroyed during the drilling. The end plates comprise very hard bone and help to give the vertebral bodies needed strength. With the end plates destroyed, the cylindrical device is now harder than the bone of the vertebral bodies and the vertebral bodies tend to collapse, "telescope," together. The telescoping causes the length of the vertebral column to shorten and can cause damage to the spinal cord and nerves that pass between the two adjacent vertebrae.

It is desirable to have a fixation device which not only eliminates the need to implant pedicle screws into the vertebrae but also which connects to the strong anterior vertebral bodies. The device should be easy to place and should prevent potentially damaging telescoping of adjacent vertebrae.

SUMMARY OF THE INVENTION

The present invention provides an anterior stabilization device which provides fixation and stabilization at both the anterior margin of the vertebral body and in the anterior column. The device comprises a hollow, generally oval shaped spacer and a retaining plate. The spacer comprises a side wall and porous superior and inferior walls, which are preferably dome-shaped. Along the anterior side of the spacer there are provided at least one superior lip which extends upwardly, i.e., in a superior direction, from the side wall and at least one inferior lip extending downwardly, i.e. in an inferior direction from the side wall, each lip containing a screw hole for receiving a non-weight bearing bone screw. Preferably there are three lips, i.e., two inferior lips and one superior lip or two superior lips and a single inferior lip. In a preferred embodiment of the invention, the spacer comprises an anterior extension from which the superior and inferior lips extend.

Access means are provided for loading the interior of the spacer with bone graft, bone morphogenic protein or the like. One preferred access means comprises one or more openings in the side wall on the anterior side of the spacer. Another preferred access means comprises a removably attachable superior and/or inferior wall.

The retaining plate is fixedly attachable to the anterior side of the spacer by means of a set screw or the like. The retaining plate is configured such that, when attached, it covers at least a portion of the head of any bone screw which is positioned in the screw holes of the superior and inferior lips to thereby prevent the screw from backing out. The retaining plate may also cover some or all of any access opening in the side wall.

The device of the present invention may be used to stabilize any portion of the spine, e.g., cervical, thoracic or lumbar. The device is sized according to the particular intervertebral disk which it replaces. Generally the spacer will have a height of from about 7 to about 14 mm, a lateral width of from about 10 to about 32 mm and an anterior-posterior width of from about 10 to about 30 mm. Spacers designed for cervical and thoracic use will typically have a height of from about 7 to about 10 mm, a lateral width of from about 13 to about 17 mm and an anterior-posterior width of from about 10 to about 14 mm. Spacers designed for lumbar use typically have a height of from about 8 to about 14 mm, a lateral width of from about 26 to about 32 mm and an anterior-posterior width of from about 22 to about 30 mm.

BRIEF DESCRIPTION OF THE DRAWINGS

Embodiments of the invention will now be described with reference to the following drawings which:

FIG. 4 is a lateral anterior view of an intervertebral spacer of the device of FIG. 1;

FIG. 5 is a posterior view of an intervertebral spacer of the device of FIG. 1;

FIG. 10 is a lateral view of a lordotic vertebral spacer made in accordance with the present invention;

FIG. 11 is a lateral view of a kyphotic vertebral spacer made in accordance with the present invention;

FIG. 12 is a posterior view of a scoliotic spacer with a left to right angle;

FIG. 13 is a posterior view of a scoliotic spacer with a right to left angle;

FIG. 14 is an exploded perspective view of another preferred anterior stabilization device made in accordance with the present invention;

DETAILED DESCRIPTION

The following is a list of definitions that apply to this application:

Anterior—situated in front of or in the forward part of an organ or structure; pertaining to the front surface.

Inferior—situated below; directly downward; pertaining to the bottom surface; closest to the tail.

Lateral—denoting a position farther from the median plane or midline of the body or of a structure; pertaining to a side surface.

Posterior—situated in back of or in the backward part of an organ or structure; pertaining to the back surface.

Superior—situated above; directly upward; pertaining to the top surface; closest to the head.

Figure 1:
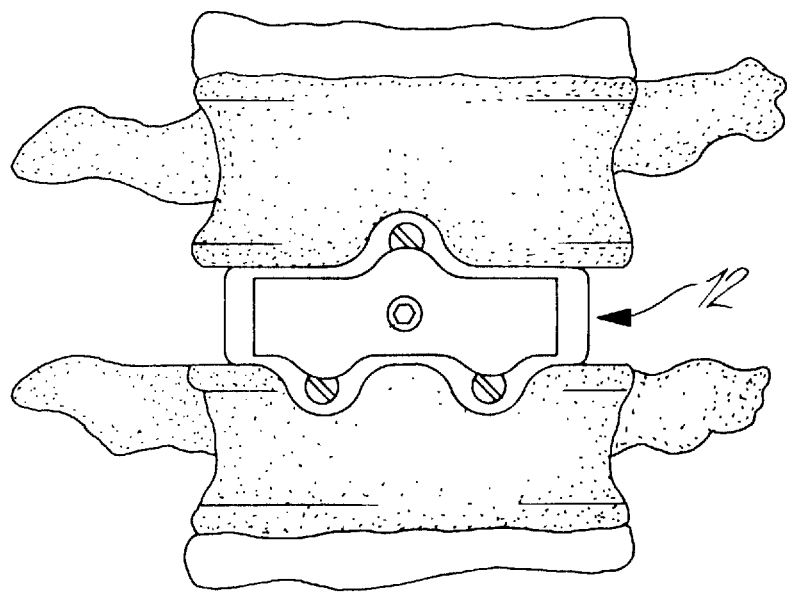
FIG. 1 is an anterior view of the lumbar spine with the present invention inserted between two adjacent vertebral bodies.

Turning in detail to the drawings where like reference numerals designate identical or corresponding parts throughout the several views and different embodiments, FIG. 1 illustrates an anterior view of two lumbar vertebrae with a preferred anterior fixation device 12 made in accordance with the present invention installed. The intervertebral disc that normally is between the two vertebrae has been replaced with the anterior fixation device. Besides the lumbar spine, the anterior fixation device can also be used in the cervical spine and the thoracic spine.

Figure 1A:
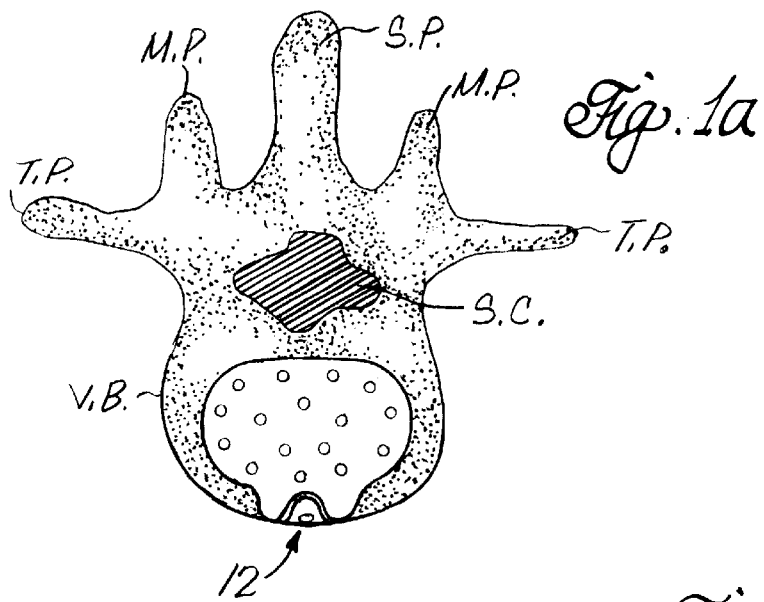
FIG. 1a is a superior view of a lumbar vertebra with the present invention placed over the vertebral body.

FIG. 1a is a superior view of the anterior fixation device 12 located on the superior surface of a lumbar vertebra. As illustrated in FIG. 1a, the anterior fixation device is primarily centered within the vertebral body, V.B., of the lumbar vertebra. The spinal cord, S.C., is located posteriorly from the anterior fixation device. The spinous process, S.P., is the most posterior pat of the vertebra. The mammillary processes, M.P., are lateral to the spinous process and the transverse processes, T.P., are located on the lateral sides of the vertebra.

Figure 1B:
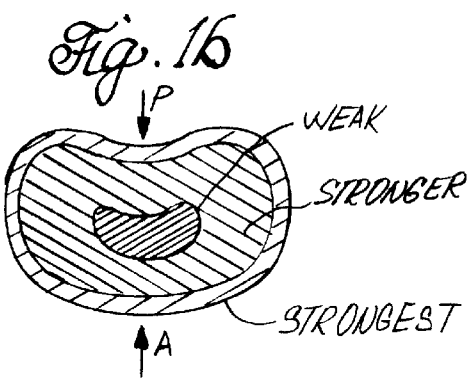
FIG. 1b is a superior view of a vertebral body.

FIG. 1b is a cross section of a vertebral body illustrating the relative strengths of the bone within the vertebral body. The vertebral body is essentially oval shaped. The anterior surface, A, and the posterior surface, P, are indicated. In the center of the vertebral body is a generally weak area of bone that comprises mostly cancellous bone. A ring shaped area surrounding the weakest area of the bone comprises stronger cortical bone. The outermost ring of the vertebral body comprises annular apophyses, the strongest bone. As will be detailed below, the anterior fixation device is shaped to utilize the stronger areas of the vertebral body for support. Additionally, relatively short bone screws are placed through the device and into the bone of the annular apophyses and the cortical bone to secure the device in place to fix the relative position of the two adjacent vertebrae.

Figure 1C:
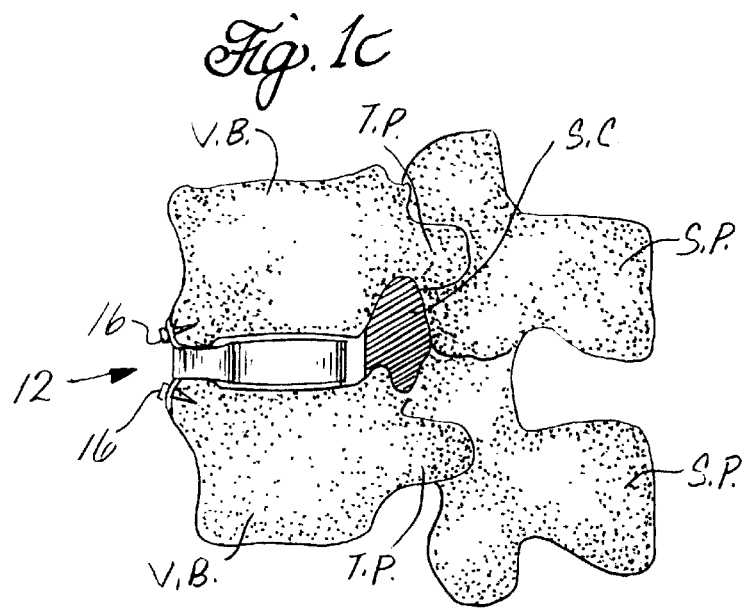
FIG. 1c is a lateral view of the lumbar spine with the present invention placed between two adjacent vertebral bodies.

FIG. 1c is a lateral view of the lumbar spine with the anterior fixation device 12 inserted in a vertebral disc space. The anterior fixation device is anchored into place by relatively short bone screws 16 on the anterior surface of two adjacent vertebral bodies. The length of the bone screws being from ¼ to ½ of the anterior-posterior dimension of the vertebral body. The bone screws 16 are placed at an angle relative to the horizontal midline plane of the anterior fixation device. The angle of placement is about 15° to about 20° from the horizontal plane. As will be described later, the angled placement of the bone screws provides the surgeon placing the device in a patient one access point from which to screw the bone screws in place.

Figure 2:
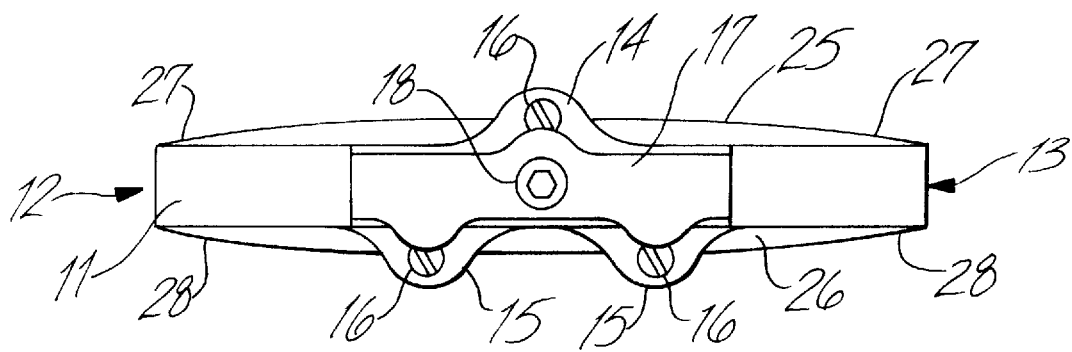
FIG. 2 is an anterior view of a preferred anterior stabilization device made in accordance with the present invention.
Figure 3:
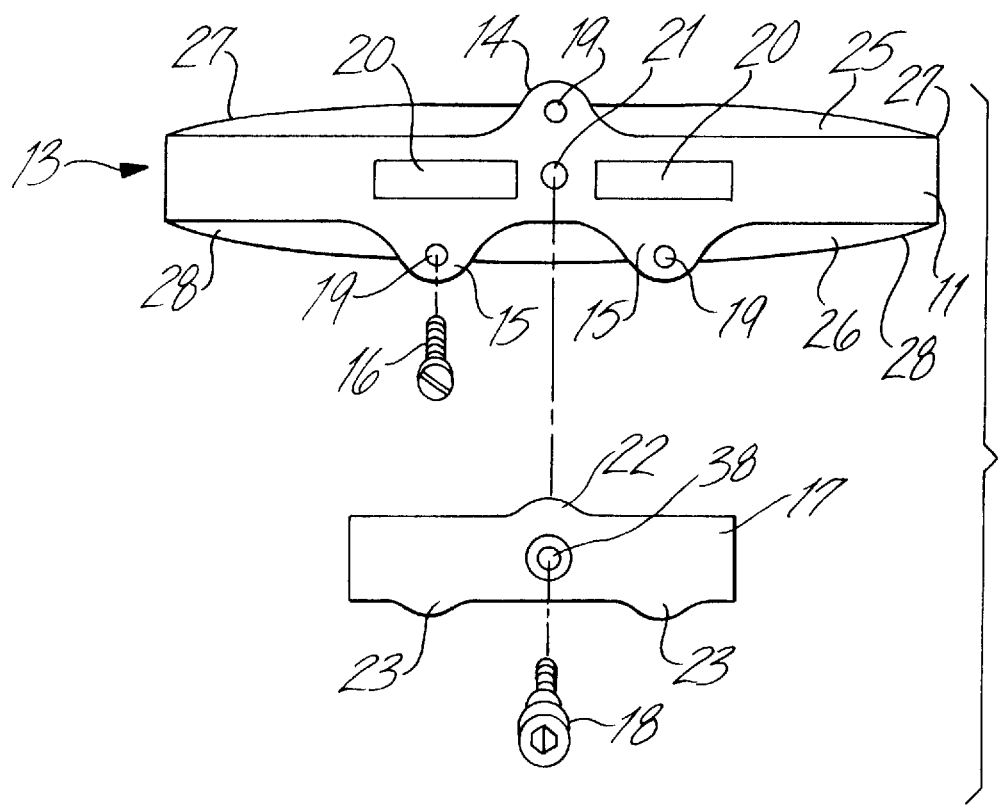
FIG. 3 is an exploded anterior view of the device of FIG. 2.

The complete anterior fixation device 12 is better illustrated in FIGS. 2 and 3. The anterior fixation device comprises an intervertebral spacer 13 (also referred to herein simply as a spacer)having a generally vertical side wall 11 which has a generally oval cross sectional shape, a generally dome-shaped porous superior wall 25 with tapered sections 27 about its periphery, a generally dome-shaped inferior porous wall 26 with tapered sections 28 around its periphery, a superior lip 14 and two inferior lips 15. Each lip 14 and 15 has a screw hole 19 through which a bone screw 16 may pass. A retaining plate 17 is attached to the spacer 13 by a set screw 18.

The intervertebral spacer 13 can be made out of any suitable material that is well known in the art. Preferably, the spacer will be made out of titanium or an alloy of titanium. The spacer is a hollow structure with walls that are preferably about 1 to 2 mm thick. As can be seen in FIG. 3, the side wall of the spacer 13 has access openings 20 on both sides of a threaded set screw aperture 21. The openings 20 allow access into the interior of the hollow spacer.

On the superior lip 14 and inferior lips 15 are screw holes 19 that bone screws 16 can be inserted through and into the annular apophysis and cortical bone of a vertebral body. The bone screws can be made out of any suitable material that is well known in the art. Preferably, the bone screws will be made out of the same material as the spacer, which in the preferred embodiment is titanium or an alloy of titanium. In the preferred embodiment, the bone screws are round head screws that may be screwed into the bone of the vertebral bodies with a flat head screwdriver. Other types of bone screws can also be used.

Figure 6:
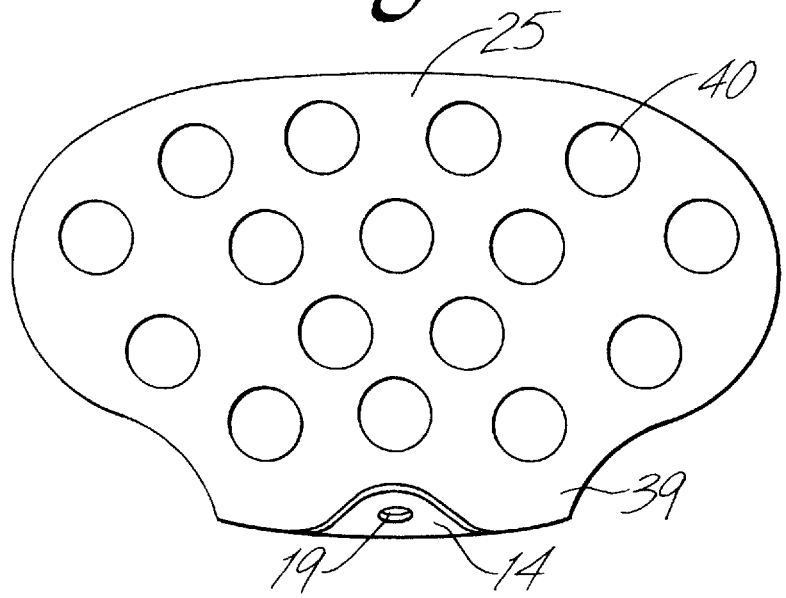
FIG. 6 is a superior view of the intervertebral spacer of the device of FIG. 1.
Figure 7:
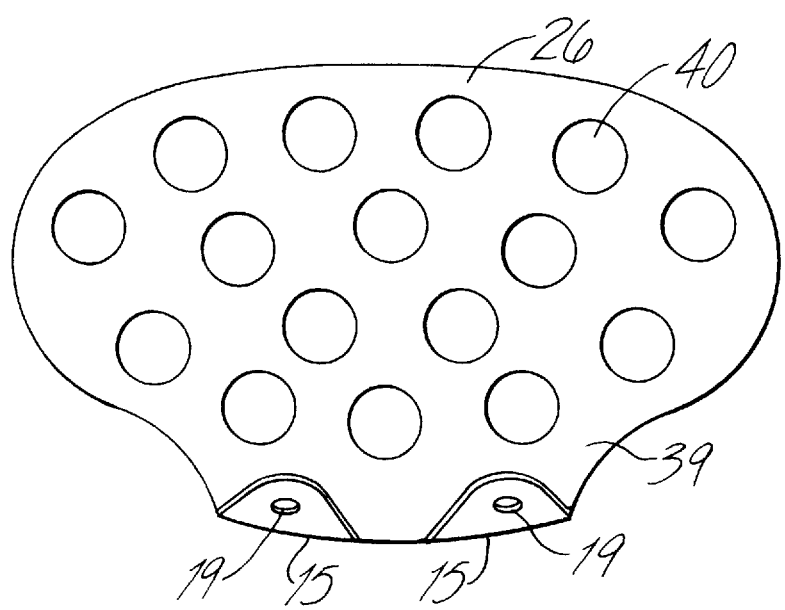
FIG. 7 is an inferior view of the intervertebral spacer of the device of FIG. 1.

Referring to FIGS. 6 and 7, the intervertebral spacer 13 is essentially oval in shape with the anterior portion of the oval having an extension 39 to allow for the spacer to be anchored over anterior annular apophyses of two adjacent vertebral bodies. The anterior edge of the extension 39 has a curved superior lip 14 that has a screw hole 19 sized such that a bone screw can be inserted therethrough. As illustrated in FIGS. 4 and 6, the superior lip 14 is curved posteriorly for placement over an annular apophysis of a vertebral body. The superior wall is preferably porous, i.e., comprises pores or holes, to allow for bone to grow through the pores or holes to fuse the two vertebra together. As illustrated, the superior surface could be made porous by drilling a plurality of holes 40 through the surface. Additionally, a porous material such as Hydracell supplied by Danek Medical, Inc. can be used.

Referring now to FIGS. 4, 5 and 7, the inferior wall 26 is illustrated with inferior lips 15 and screw holes 19 therethrough. As with the superior lip 14, the inferior lips 15 are curved posteriorly such that the inferior lips 15 can be anchored to a vertebral body annular apophysis. The inferior wall is a mirror image of the superior wall and is preferably also made porous. In the preferred embodiment, holes 40 are drilled through the surface.

In the preferred embodiment there are three lips, one superior and two inferior, that form a triangle shape and provide three points of fixation to the vertebral bodies. The triangulation provides an additional benefit in that the spacers can easily stack on top of each other such that a series of adjacent vertebrae can be fixed together using the spacers of the present invention. As would be appreciated by a person skilled in the art, four or more points of fixation to the vertebral bodies could also be used.

In FIG. 4, the midline 29 of the larger diameter of the oval part of the spacer 13 is illustrated. In use, the midline 29 is along the midline of the larger diameter of two adjacent oval shaped vertebral bodies. As can be seen in FIGS. 4 and 5, the superior wall 25 has tapered surfaces 27 about its outer periphery and the inferior wall 26 has tapered surfaces 28 about its outer periphery. As will be discussed below, the tapered superior and inferior surfaces allows the surgeon easier placement during a surgical procedure. Additionally, the tapered surfaces provide greater stability of the device once installed.

In an alternate embodiment, the superior and inferior walls have lateral ridges (not shown) spanning across the anterior half of the oval shaped spacer. The lateral ridges provide resistance against the device slipping forward after the surgical installation of the spacer.

Figure 8:
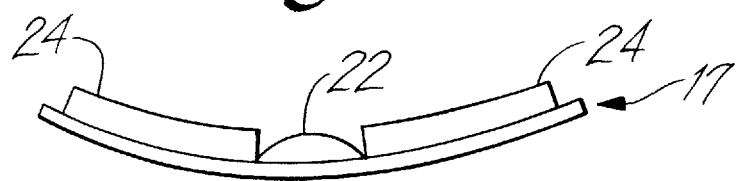
FIG. 8 is a superior view of a retaining plate of the device of FIG. 1.
Figure 9:
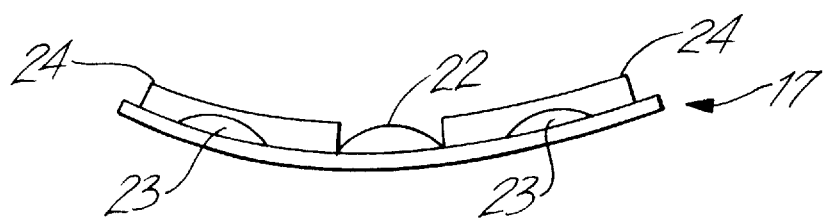
FIG. 9 is an inferior view of a retaining plate of the device of FIG. 1.

Referring now to FIGS. 3, 8 and 9, a retaining plate 17 is illustrated. The retaining plate can be made from any suitable material well known in the art. Preferably, the retaining plate will be made out of the same material as the intervertebral spacer, which in the preferred embodiment is titanium or a titanium alloy. The retaining plate is curved to fit the curvature of the anterior surface of the intervertebral spacer 13. In the center of the retaining plate is a tapered aperture 39 that is sized to allow a set screw 18 to be inserted therethrough with the head of the set screw retained in the tapered aperture. The retaining plate has a superior retaining lip 22 and two inferior retaining lips 23. When the retaining plate 17 is in place on the intervertebral disc spacer 13, the superior retaining lip 22 partially covers the head of a bone screw extending through the superior lip of the intervertebral spacer and the inferior retaining lips 23 partially cover the heads of bone screws extending through the inferior lips of the intervertebral spacer.

As illustrated in FIGS. 8 and 9, the posterior surface of the retaining plate has two rectangular shaped flanges 24. The flanges are located laterally with respect to the tapered set screw aperture 38. The flanges extend outward from the posterior surface of the retaining plate 1 to 2 mm. The rectangular shaped flanges are sized to matingly fit into the rectangular access openings 20 of the intervertebral spacer when the retaining plate is in place. Thus, as illustrated in FIG. 2, when the retaining plate 17 is secured to the spacer with the set screw 18 screwed into the threaded aperture 21 of the spacer, the bone screws 16 cannot back out from the spacer. The set screw 18 is secured to the spacer and is tightened accordingly to prevent loosening. The set screw is preferably any suitable material well known in the art, preferably titanium or a titanium alloy. In the preferred embodiment, the set screw is an hexagonal set screw that is placed with an hexagonal driver. Other types of set screws can be used.

As would be appreciated by a person skilled in the art, the shape and size of the opening 20 in the spacer may vary. If other shapes or sizes are used, then varying sized and shaped retaining plates would also be used.

The dimensions of the intervertebral spacer vary depending on the intended use of the spacers, having small spacers for the cervical spine, medium spacer for the thoracic spine, and large spacers for the lumbar spine. For the cervical and thoracic spine, spacers having a range of heights of about 7, 8, 9, or 10 mm are preferred. The lateral side to side dimensions of the largest lateral diameter of the spacers are preferably about 13, 15 and 17 mm. The anterior-posterior dimension of the cervical and thoracic spacers are preferably about 10, 12 and 14 mm. The spacers in the lumbar spine also have varying dimensions. The heights of the lumbar spacers are preferably about 8, 10, 12 and 14 mm. The lateral dimensions of the lumbar spacers are preferably about 26, 28, 30, and 32 mm. The anterior-posterior dimensions of the lumbar spacers are preferably about 22, 24, 26, 28, and 30 mm. The retaining plates would be sized appropriately to fit the varying heights and lateral dimensions of the varying sized spacers.

FIG. 10 illustrates an alternative embodiment to the present invention. A spacer 30 with a lordotic angle, a, is illustrated. The lordotic angle extends from a smaller posterior surface, P, to a larger anterior surface, A. The angle, a, can range from about 1° to about 45°. Similar reference numerals are used to indicate the superior wall 25 with tapered sections 27, the inferior wall 26 with tapered sections 28, the superior lip 14 and inferior lip 15.

FIG. 11 illustrates a kyphotic spacer 31. In this embodiment the kyphotic spacer has a superior wall 25, and inferior wall 26, a superior tapered section 27 and inferior tapered section 28, an additional superior tapered section 34 and inferior tapered section 35 on the anterior surface of the spacer. The kyphotic angle, b, from a smaller anterior surface, A, to a larger posterior surface, P, the kyphotic angle ranging from about 1° to about 45°. Additionally illustrated on the anterior surface is an optional smaller kyphotic angle, b'. The angle b' represents the kyphotic angle of the anterior extension 39 of the spacer. The kyphotic angle b' will be from about 1° to about 10° less than the kyphotic angle b.

FIG. 12 is a posterior view of a scoliotic intervertebral spacer 32. In this particular embodiment the scoliotic angle, c, is from a smaller left lateral side to a larger right lateral side. Angle c range from about 1° to about 45°. The retaining plate would also be appropriately angled.

FIG. 13 is a posterior view of a scoliotic spacer with a scoliotic angle, d, from a smaller right lateral surface to a larger left lateral surface. Angle d ranges from about 1° to about 45°. The retaining plate would also be appropriately angled.

Figure 15:
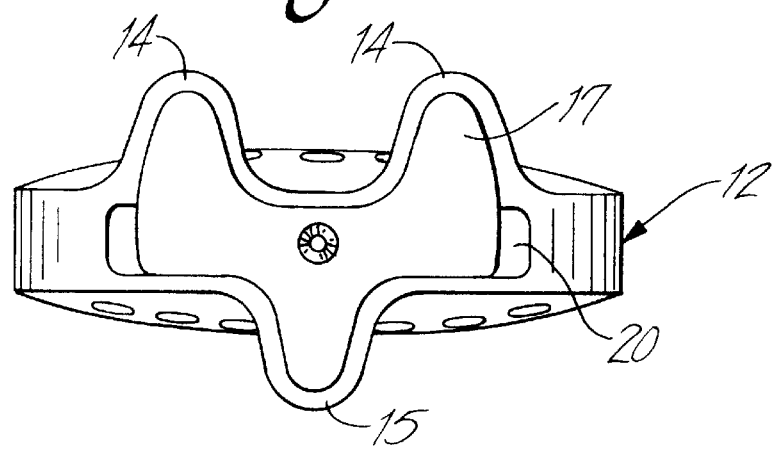
FIG. 15 is an anterior side view of the device of FIG. 14.

FIGS. 14 and 15 show an alternate embodiment of the invention wherein the screw holes 19 in the superior and inferior lips 14 and 15 are located in recesses 40. The retaining plate 17 comprises superior and inferior retaining lips 22 and 23 which have the same shape as and nest in the recesses of the lips 14 and 15 when the retaining plate is installed.

Figure 16:
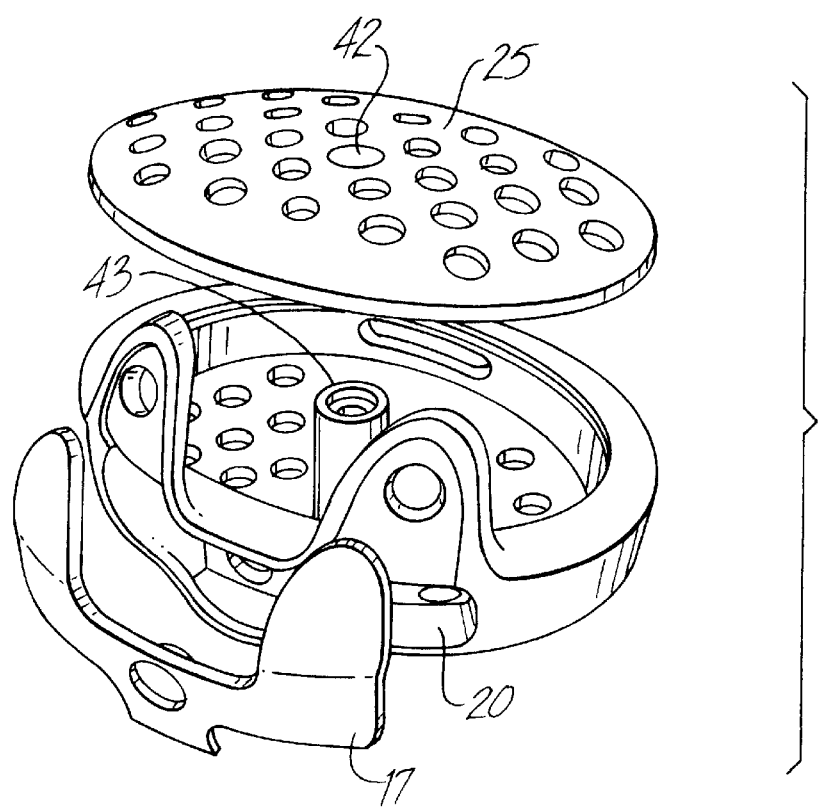
FIG. 16 is an exploded perspective view of yet another preferred anterior stabilization device made in accordance with the present invention.

FIG. 16 shows yet another embodiment of the invention. In this embodiment, the superior wall 25 is removable. This allows the hollow interior of the spacer to be packed with bone grafts, bone morphogenic protein or the like before insertion of the spacer into the intervertebral disk space. The top plate is fixedly attachable to the rest of the spacer by means of a set screw (now shown) which extends through the superior wall 25 through screw hole 42 into a threaded post 43. It is understood that the inferior wall may be removable instead of or in addition to the top wall. Alternatively, only a portion of the superior and/or inferior wall may be removable. Further, a removable superior and/or inferior wall may replace access openings 20 or may be present in addition to access openings 20.

The present invention is designed to be manufactured as a kit with multiple sized spacers and retaining plates present in the kit as well as multiple lordotic, kyphotic and scoliotic spacers. Thus, a surgeon who is performing an anterior fixation surgery can isolate the anterior spine using well known surgical techniques and place an appropriate sized and shaped spacer from the kit into the intervertebral space of two adjacent vertebrae. If the spacer used is too large, too small, or the wrong shape that spacer can be removed and replaced with a spacer of a more appropriate size and shape.

Figure 17:
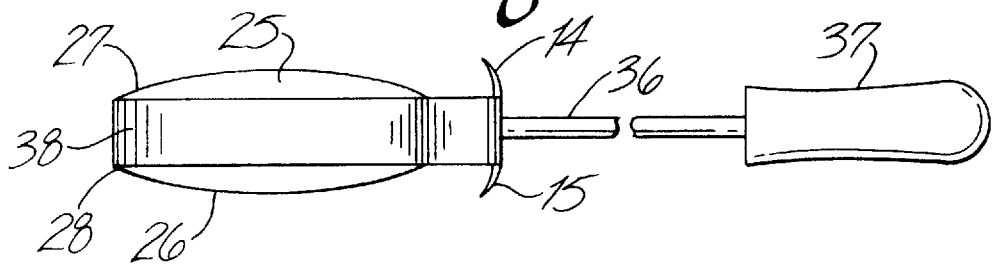
FIG. 17 is a lateral view of an intervertebral spacer connected to a stem and a handle.
Figure 18:
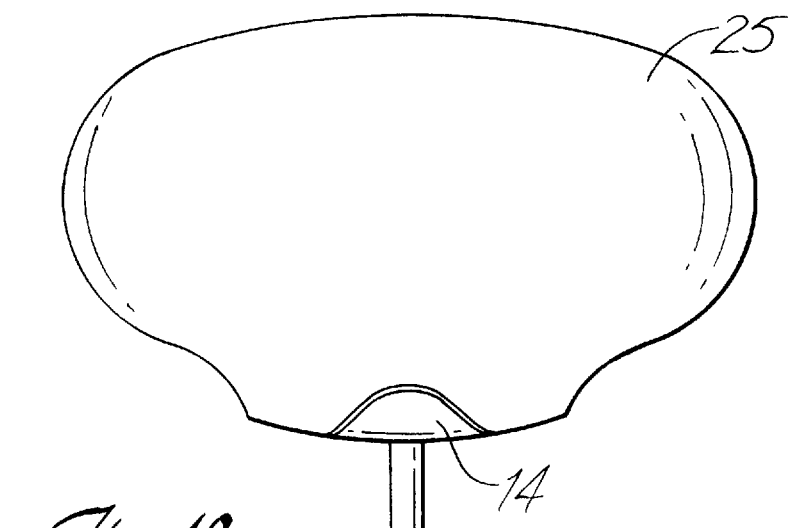
FIG. 18 is a superior view of an intervertebral spacer connected to a stem and a handle.

FIGS. 17 and 18 illustrate a specialized tool, a "spacer sizer," used for appropriate sizing of the intervertebral spacer. An intervertebral spacer 38 is fixedly attached to a stem 36 which is attached to a handle 37 of the spacer sizer. The stem extends from the center of the anterior surface of the spacer. Alternatively, a placement tool with a handle 37 and a threaded end extending from the stem 36 that can be threaded into the threaded set screw aperture 21 of the intervertebral spacer is provided. The stem 36 would be of sufficient length to allow the surgeon easy placement into the intervertebral disk space of the spine. In the surgical kit described above, there would be included a set of spacer sizers corresponding to the different shaped and sized spacers. Alternatively, the kit would include the threaded placement tool to be threaded into different sized and shaped spacers for surgical placement.

The following is a description of the use of the anterior fixation device of the present invention. A patient needing spinal fixation or fusion would be prepped appropriately for anterior spine surgery. The surgeon would then use standard anterior surgical approaches to isolate two or more vertebral bodies to be treated. The intervertebral disc would then be removed and a curette or similar surgical instrument would prepare the vertebral body end plates for receiving the anterior fixation device. The end plates would be lightly scraped or drilled, with the majority of the scraping occurring in the center of the vertebral body end plate. The end plate scrapings generate a tapered pocket for placement of the tapered anterior fixation device. The tapering helps to ensure proper placement of the anterior fixation device and helps to maintain the device in place.

Once a tapered pocket has been created, the surgeon then selects a spacer sizer as illustrated in FIGS. 14 and 15 to size the pocket and to select the appropriately sized spacer. With the spacer sizer in place in the pocket between two adjacent vertebrae, the surgeon would take appropriate X-rays to check the size of the spacer and the pocket and its location. If a larger, smaller or different shaped spacer is needed, the surgeon would remove the spacer sizer and replace it with a more appropriate spacer sizer until a proper size is confirmed by X-ray. In the alternative, the surgeon would thread a spacer onto the threaded stem of the placement tool and then place that spacer into the pocket with the tool attached. The shape and size of the spacer would then be confirmed with X-ray. If a different spacer is needed, the tool is removed with the spacer attached, the spacer is then unscrewed from the handle and replaced with a different spacer. Once confirmation of the shape and size occurs using X-ray, the surgeon then unscrews the tool from the spacer leaving the spacer in the pocket between the adjacent vertebrae.

The surgeon next secures the spacer to the adjacent vertebrae using the bone screws. As indicated above, the bone screws are preferably angled away from the horizontal plane of the spacer. Thus, all three bone screws can be driven into the annular apophyses and cortical bone of the vertebral bodies using one axial access point. The use of only one access point is advantages, especially in the cervical spine, where there is limited maneuvering room.

The interior of the spacer is then filled with bone grafts, bone morphogenic protein, or the like, using the anterior openings to the spacer. The retaining plate is then placed over the anterior spacer openings and the set screw is then driven into place to secure the retaining plate to the spacer. Alternatively, if the superior and/or inferior wall is removable, the spacer is filled with bone grafts, bone morphogenic protein or the like before placement of the spacer in the intervertebral disk space.

If three or more adjacent vertebrae are to be treated, the surgeon would remove the next intervertebral disc and then repeat the above procedure to surgically place another anterior fixation device. As can be appreciated, the spacers are designed to stack one on top of the other such that the entire spine could be fixed. The singular superior lip of a spacer attached to the inferior annular apophysis of a vertebral body fits between the two inferior lips of another spacer attached to the superior annular apophysis of the same vertebral body.

Once the spinal column has been appropriately treated, the surgeon then finishes the anterior surgery using well known surgical techniques.

The anterior stabilization device of the present invention provides a number of unique advantages. The device provides stability by fixation both in the anterior column by means of the bone screws at the anterior margin of the vertebral body and in the intervertebral disk space by means of the spacer and subsequently by means of fusion. Conventional anterior plates fix only at the anterior portion of the vertebral body. Conventional cages provide only stabilization in the intervertebral disk area.

In conventional anterior plates, rigidity is derived either from biocortical purchase of bone or by locking the screw head to the plate. This creates a rigid box-like structure which can prevent desirable weight bearing on bone grafts in the intervertebral disk space which, in turn, may prevent fusion. The present invention overcomes this potential disadvantage. In the present design, the bone screws are non-weight herring. Due to the presence of the retaining plate, the bone screws are allowed to toggle within the screw holes of the spacer without worry of backout. Hence, the present design allows non-weight bearing screws to maintain positional fixation at the anterior margin while at the same time allows weight bearing support onto the intradiscal portion of the device.

The presence and design of the retaining plate contributes to the unique advantages of the present invention. Conventional devices that lock screws in place are designed to be weight bearing and to provide a rigid structure. With such designs, there is a risk of screw breakage, screw backout and, as described above, bone fusion failure. By means of the design described herein, the bone screws do not create a rigid structure and are non-weight bearing, thereby eliminating the risk of breakage. Moreover, by use of a retaining plate as described herein, risk of screw backout is eliminated.

Another advantage of the present design is that the bone screws are anchored in the hardest portions of the vertebra, thereby providing the greatest structural support. Conventional anterior plates place long bone screws into the mid body area of the vertebra which provides less overall structural support.

Thus, an anterior fixation device is disclosed which allows the surgeon to spatially fix two or more adjacent vertebral bodies together at both the anterior margin and the intervertebral disk portions of the vertebral body. The device uses relatively small, non-weight bearing bone screws that cannot extend into the spinal canal. The device is easy to place and prevents potentially damaging telescoping of the fixed vertebral bodies.

While embodiments and applications of this invention have been shown and described, it would be apparent to those skilled in the art that many more modifications are possible without departing from the inventive concepts herein. The invention, therefore, is not to be restricted except in the spirit of the appended claims.

What is claimed is:

1. An anterior stabilization device comprising:
   a generally hollow intervertebral spacer having anterior and posterior sides and comprising:
      a side wall having a generally oval cross-sectional shape;
      a porous superior wall;
      a porous inferior wall;
      at least one superior lip extending upwardly above the side wall at the anterior side of the spacer;
      at least one inferior lip extending downwardly below the side wall at the inferior side of the spacer;
      a screw hole in each superior and inferior lip; and
      access means for allowing insertion of bone graft material into the hollow interior of the spacer; and
   a retaining plate fixedly attachable to the anterior side of the spacer, said retaining plate being sized to cover at least a portion of the head of each bone screw which is inserted through screw holes of each superior and inferior lip.

2. An anterior stabilization device as claimed in claim 1 wherein the spacer further comprises an anterior extension and wherein the superior and inferior lips extend upwardly and downwardly from the anterior extension.

3. An anterior stabilization device as claimed in claim 1 wherein each of the superior and inferior walls are dome-shaped.

4. An anterior stabilization device as claimed in claim 1 wherein the spacer has a height of from about 7 to about 14 mm.

5. An anterior stabilization device as claimed in claim 1 wherein the spacer has a lateral width of from about 13 to about 32 mm.

6. An anterior stabilization device as claimed in claim 1 wherein the spacer has an anterior-posterior width of from about 10 to about 30 mm.

7. An anterior stabilization device as claimed in claim 1 wherein the spacer comprises two inferior lips and one superior lip.

8. An anterior stabilization device as claimed in claim 1 wherein the access means comprises at least one opening in the side wall at the anterior side of the spacer.

9. An anterior stabilization device as claimed in claim 1 wherein the access means comprises a removably attachable superior wall.

10. An anterior stabilization device as claimed in claim 1 wherein the access means comprises a removably attachable inferior wall.

11. An anterior stabilization device as claimed in claim 1 wherein the spacer is sized to fit within the intervertebral disk space between two adjacent cervical vertebrae.

12. An anterior stabilization device as claimed in claim 1 wherein the spacer is sized to fit within the intervertebral disk space between two adjacent thoracic vertebrae.

13. An anterior stabilization device as claimed in claim 1 wherein the spacer is sized to fit with the intervertebral disk space between two adjacent lumbar vertebrae.

* * * * *